(12) United States Patent
Nallakrishnan et al.

(10) Patent No.: US 12,042,430 B2
(45) Date of Patent: Jul. 23, 2024

(54) SURGICAL INSTRUMENT AND METHOD FOR GONIOTOMY PROCEDURE

(71) Applicant: RAICO International, LLC, Westmont, IL (US)

(72) Inventors: Ravi Nallakrishnan, Willowbrook, IL (US); Mitsunobu Yokoyama, Hiroshima (JP)

(73) Assignee: RAICO International, LLC, Westmont, IL (US)

( * ) Notice: Subject to any disclaimer, the term of this patent is extended or adjusted under 35 U.S.C. 154(b) by 920 days.

(21) Appl. No.: 16/919,401

(22) Filed: Jul. 2, 2020

(65) Prior Publication Data
US 2021/0000648 A1    Jan. 7, 2021

Related U.S. Application Data

(60) Provisional application No. 62/870,383, filed on Jul. 3, 2019.

(51) Int. Cl.
*A61F 9/007* (2006.01)
*A61H 9/00* (2006.01)

(52) U.S. Cl.
CPC ........ *A61F 9/00781* (2013.01); *A61H 9/0071* (2013.01); *A61H 2201/0153* (2013.01)

(58) Field of Classification Search
CPC ............... A61H 5/00; A61H 2205/024; A61H 2201/169; A61H 2201/0153; A61N 7/00; A61N 2007/0073; A61F 9/00781; A61F 9/00; A61F 9/00745; A61F 2009/00868; A61F 2009/00891; A61F 9/007; A61B 2017/320008
See application file for complete search history.

(56) References Cited

U.S. PATENT DOCUMENTS

| | | | | |
|---|---|---|---|---|
| 5,921,998 A * | 7/1999 | Tano | ................. | A61F 9/00736 606/162 |
| 8,540,659 B2 * | 9/2013 | Berlin | ................. | A61F 2/15 604/8 |
| 2001/0053873 A1 * | 12/2001 | Schaaf | ................. | A61F 9/00781 600/166 |
| 2006/0276759 A1 * | 12/2006 | Kinast | ................. | A61M 5/3286 29/2.25 |
| 2007/0282348 A1 * | 12/2007 | Lumpkin | ............ | A61F 9/00736 606/107 |
| 2008/0051681 A1 * | 2/2008 | Schwartz | ............ | A61F 9/00781 601/2 |
| 2013/0211395 A1 * | 8/2013 | Schwartz | ............ | A61F 9/00781 606/28 |
| 2018/0104514 A1 * | 4/2018 | Gertner | ............ | A61H 23/0245 |
| 2018/0193191 A1 * | 7/2018 | Dam-Huisman | ....... | A61F 9/007 |

* cited by examiner

*Primary Examiner* — Kai H Weng
(74) *Attorney, Agent, or Firm* — Wood, Phillips, Katz, Clark & Mortimer

(57) ABSTRACT

An ophthalmic surgical instrument includes an instrument hand grip portion having an elongated configuration with proximal and distal ends, and a tip portion extending from the distal end. The tip portion has the form of an elastomeric element having a base secured to the distal end of the hand grip portion and a free end extending from the base. The free end is configured for massaging the trabecular meshwork and outer wall of the canal of Schlemm in the eye to improve aqueous outflow for the reduction of intraocular pressure.

1 Claim, 9 Drawing Sheets

SURGICAL INSTRUMENT AND METHOD FOR GONIOTOMY PROCEDURE

FIELD OF THE INVENTION

The present invention relates to a surgical instrument for performing ophthalmological procedures for treatment of eye diseases, such as glaucoma, and more particularly to a goniotomy surgical instrument having a tip portion with an elastomeric element having a roughened surface to massage the outer wall of the Schlemm's canal within the anterior chamber of the eye.

BACKGROUND OF THE INVENTION

A goniotomy is a surgical procedure primarily used to treat congenital glaucoma. It is caused by a developmental arrest of some of the structures within the anterior (front) segment of the eye. These structures include the iris and the ciliary body, which produces the aqueous fluid needed to maintain the integrity of the eye. These structures do not develop normally in the eyes of patients with isolated congenital glaucoma. Instead, they overlap and block the trabecular meshwork, which is the primary drainage system for the aqueous fluid. As a result of this blockage, the trabecular meshwork itself becomes thicker and the drainage holes within the meshwork are narrowed. These changes lead to an excess of fluid in the eye, which can cause increased pressure that can damage the internal structures of the eye and cause glaucoma.

The purpose of a goniotomy is to clear the obstruction to aqueous outflow from the eye, which in turn lowers the intraocular pressure (IOP). Lowering the IOP helps to stabilize the enlargement of the cornea and the distension and stretching of the eye that often occur in congenital glaucoma. The size of the eye, however, will not return to normal. Most importantly, once the aqueous outflow improves, damage to the optic nerve is halted or reversed. The patient's visual acuity may improve after surgery.

The goniotomy procedure can restore normal drainage of aqueous humor from the eye by removing a full thickness segment of the trabecular meshwork, thus allowing the aqueous humor to drain through the open area from which the strip of trabecular meshwork has been removed. The goniotomy procedure and certain prior art instruments useable to perform such procedure are described In U.S. Pat. No. 6,979,328 and U.S. Patent Application Publication No. US 2018/0289544 A1, each of one of which is hereby incorporated by reference herein in its entirety.

At present there remains a need in the art for the development of simple, inexpensive and accurate instruments useable to perform the procedure of massaging the tissues of the eye, including the trabecular meshwork and/or the canal of Schlemm to loosen or free deposits to assist in the restoration and/or improvement of the drainage of the eye.

SUMMARY OF THE INVENTION

In accordance with the present invention, a surgical instrument is disclosed which is particularly configured to facilitate performing a goniotomy such as for the treatment of glaucoma. The instrument includes a hand grip portion having an elongated configuration, with a proximal end and a distal end. The instrument further includes a tip portion which extends from, and which is operably connected with, the distal end of the hand grip portion. The tip portion has the form of an elastomeric element having a base that is secured to the distal end of the hand grip portion and a free end extending from the base. The free end includes at least one protrusion extending laterally outwardly therefrom for engaging the eye.

In another aspect of the present invention, the free end includes a plurality of protrusions extending from opposite, lateral surfaces and/or top and bottom surfaces thereof.

In still another aspect of the present invention, the free end includes a relatively abrasive surface. In one preferred form of the invention, the at least one protrusion extends from the relatively abrasive surface.

In another aspect of the present invention, the abrasive of the free end is formed from an impregnated abrasive composition within or atop the elastomeric element. In one presently preferred form of the invention, the abrasive composition comprises diamond particles. In another preferred form of the invention, the relatively abrasive surface of the free end has the form of surface-roughening.

According to yet another aspect of the present invention, the elastomeric element is silicone.

In one preferred form of the present invention, the instrument includes a plurality of protrusions, each of which extends laterally outwardly from the free end for engaging the eye, and each of which has a linear, horizontal configuration along the lateral surfaces of the free end.

In another preferred form of the present invention, the instrument includes a plurality of protrusions, each of which has a linear, vertical configuration along the lateral surfaces of the free end.

In another preferred form of the present invention, the instrument includes a plurality of protrusions, each of which has an arcuate, wave-like configuration along the lateral surfaces of the free end.

In another broad form of the present invention, the instrument includes a knife element that is movably arranged within the hand grip portion and that is movable relative to the free end of the elastomeric element between (i) a retracted position wherein the knife element is located proximally of the free end, and (ii) an operative position wherein at least a portion of the knife element is extended through and located distally beyond the free end.

In another broad form of the present invention, the instrument is assembled in combination with a vibratory handpiece connected to the hand grip portion, wherein the handpiece is configured to vibrate the free end in one of a torsional, longitudinal, and/or blended motion. In one preferred form, the handpiece is selected form on of the following handpieces: a longitudinally-vibrating phacoemulsification handpiece; a torsionally-vibrating phacoemulsification handpiece; an elliptically-vibrating phacoemulsification handpiece; a phacoemulsification handpiece configured for vibratory movement in three dimensions; a vitrectomy handpiece; a piezo electric handpiece; a solenoid valve handpiece; or a battery powered handpiece.

In another broad form of the present invention, the goniotomy surgical instrument is coupled with an irrigation supply source to provide an irrigation fluid (i) either through said instrument itself by way of one or more cannulas, or (ii) around the exterior of the instrument when coupled with an irrigation sleeve arranged around the exterior surface of the instrument. In one preferred form, the instrument is coupled with a vacuum source for aspirating fluids and/or tissues through one or more cannulas in the instrument or around the exterior of the instrument with an accompanying sheath or sleeve.

In one preferred form of the present invention, the hand grip portion of the instrument includes a reservoir for containing an irrigation fluid and a button to permit the user to selectively provide a burst or jet of irrigation fluid (i) through the instrument, or (ii) around the instrument when coupled with an irrigation sleeve arranged around a portion of the instrument.

In still another broad form of the present invention, the surgical instrument includes a hand grip portion having an elongated configuration, having proximal and distal ends and a tip portion extending from the distal end of the hand grip portion. The tip portion is comprised of an elastomeric element having a base secured to the distal end of the hand grip portion and a tapered free end extending from the base. The free end includes at least one relatively abrasive surface having at least a first zone with a first roughness and a second zone with a second roughness that is different than the first roughness.

In another broad form of the present invention, the surgical instrument includes a hand grip portion having an elongated configuration, having proximal and distal ends and a tip portion extending from the distal end of the hand grip portion. The tip portion is comprised of an elastomeric element having a base secured to the distal end of the hand grip portion and a tapered free end extending from the base. The free end includes a first relatively abrasive surface having a first roughness, and an opposite, second relatively abrasive surface having a second roughness that is different than the first roughness. In one preferred form of the present invention, the surgical instrument first relatively abrasive surface and the opposite, second relatively abrasive surface are colored differently for improved visibility by the user of the instrument.

In still another broad form of the present invention, the surgical instrument includes a hand grip portion having an elongated configuration, having proximal and distal ends and a tip portion extending from the distal end of the hand grip portion. The tip portion is comprised of an elastomeric element having a base secured to the distal end of the hand grip portion and a tapered free end extending from the base. The free end includes a first relatively abrasive surface having a first roughness, and an opposite, relatively smooth surface.

In one preferred form of the present invention, the surgical instrument free end is roughened and terminates in a blunted, semicircular shape.

In another preferred form of the invention, the first relatively abrasive surface is concave and the opposite, relatively smooth surface is convex.

In yet another preferred form of the invention, the first relatively abrasive surface is concave and the opposite, relatively smooth surface is concave.

In one form of the invention, the instrument free end is smooth and rounded between said the relatively abrasive surface and the opposite, relatively smooth surface.

In one form of the invention, the first relatively abrasive surface has a generally horseshoe shape with a closed, arcuate proximal portion and an open, distal portion.

In still another broad form of the present invention, the surgical instrument includes a hand grip portion having an elongated configuration, having proximal and distal ends and a tip portion extending from the distal end of the hand grip portion. The tip portion is comprised of an elastomeric element having a base secured to the distal end of the hand grip portion and a tapered free end extending from the base. The free end has the form of a pyramidal frustum having a pair of relatively smooth, opposite, non-abrasive top and bottom surfaces and a pair of relatively abrasive, opposite lateral surfaces. In one preferred form of the invention, the free end terminates in the form of a square that is relatively abrasive In another broad form of the present invention, the surgical instrument includes an elastomeric element that is fully retractable into the hand grip portion of the instrument and the elastomeric element may be selectively extended axially beyond the hand grip portion by a user of the instrument. According to one preferred form of the present invention, the elastomeric element extends between about 1.0 mm and about 3.0 mm beyond the hand grip portion of the instrument, and more preferably it extends between about 1.4 mm and about 1.6 mm beyond the hand grip portion.

In still another broad form of the present invention, a method for improvement of the drainage of fluid of the eye includes the step of obtaining any of the surgical instruments disclosed herein and contacting the trabecular meshwork of the eye with the free end of the elastomeric element to massage the trabecular meshwork to dislodge deposits within the meshwork.

BRIEF DESCRIPTION OF THE DRAWINGS

In the accompanying drawings forming part of the specification, in which like numerals are employed to designate like parts throughout the same, FIG. 1 shows only a distal portion of the instrument wherein the proximal portion of the instrument may have any suitable shape for being gripped by a user or connected to a machine;

FIG. 2 shows the operative, distal end of the instrument with a knife element of the instrument in a retracted position;

FIG. 3 shows a knife element of the instrument in an extended position;

FIG. 4 shows only a distal, operative portion of the instrument;

FIG. 5 shows only a distal, operative portion of the instrument;

FIG. 6 shows only a distal, operative portion of the instrument;

FIG. 7 shows only a distal, operative portion of the instrument;

FIG. 8 shows only a distal, operative portion of the instrument;

FIG. 9 shows only a distal, operative portion of the instrument;

FIG. 14 shows only a distal, operative portion of the instrument;

FIG. 17 shows only a distal, operative portion of the instrument;

FIG. 21 shows only a distal, operative portion of the instrument;

DESCRIPTION OF THE PREFERRED EMBODIMENTS

While this invention is susceptible of embodiment in many different forms, this specification and the accompanying drawings disclose only specific forms as examples of the invention. The invention is not intended to be limited to only the embodiments so described, and the scope of the invention will be pointed out in the appended claims.

Figure 1:
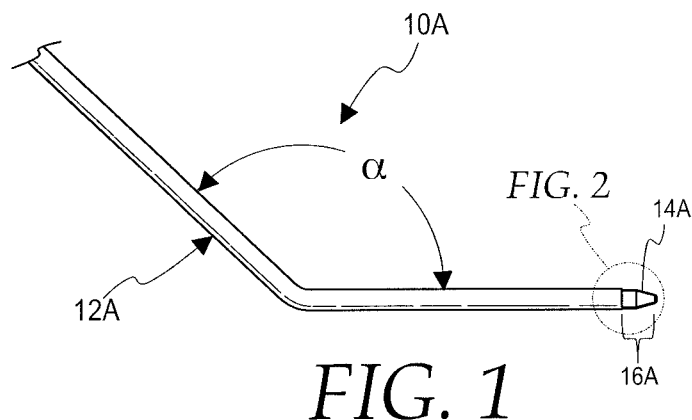
FIG. 1 is a fragmentary, side elevation view of a first embodiment of a surgical instrument according to the present invention.
Figure 2:
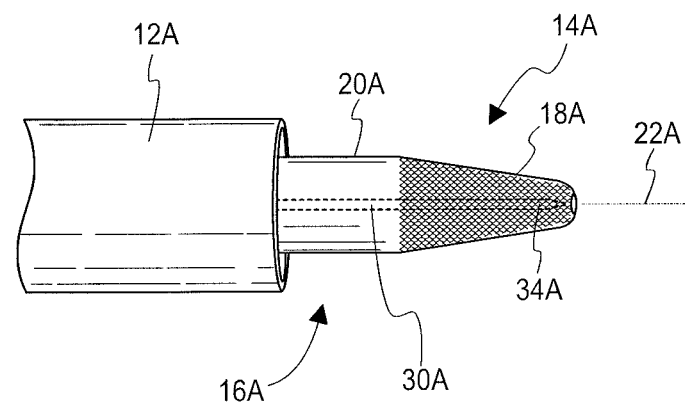
FIG. 2 is an enlarged, detailed side elevation view of the portion of the instrument circled in FIG. 1.
Figure 3:
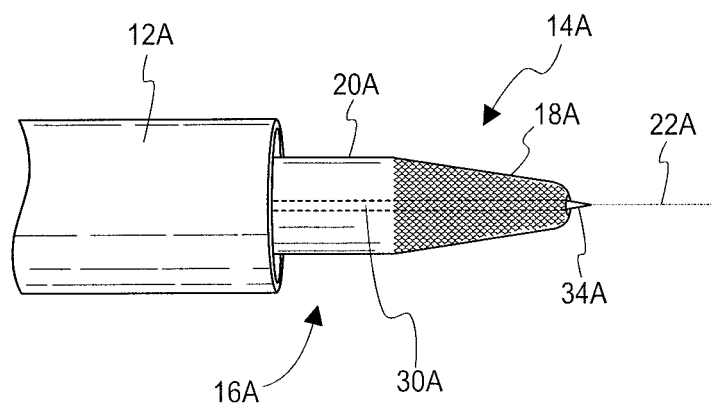
FIG. 3 is an enlarged, fragmentary, side elevation view of the instrument shown in FIG. 2.

A first embodiment of a goniotomy surgical instrument of the present invention is illustrated in FIGS. 1-3, wherein the instrument is designated generally by the reference number 10A. The first illustrated embodiment of the instrument 10A includes an elongated hand grip portion 12A for being gripped by a user of the instrument 10A, and which can be provided with either a rounded configuration as illustrated or with a flattened, polygonal, or irregular configuration (not illustrated). The hand grip portion 12A has a proximal end and a distal end.

Referring to FIG. 1, the hand grip portion 12A proximal and distal sections or portions are arranged at an obtuse angle (α) relative to each other of between about 120 degrees and about 140 degrees, and more preferably at an angle (α) of about 130 degrees.

The instrument 10A includes a specifically configured scraping or abrading tip portion 14A, extending from the distal end of the hand grip portion 12A, which facilitates scraping, rubbing, massaging, and/or abrading the tissues of the eye to permit drainage of aqueous humor to enhance the vision of the patient and to reduce pressure in the eye.

With reference to FIGS. 2 and 3, the tip portion 14A comprises an elastomeric element 16A having a base portion or base 20A secured to the distal end of the hand grip portion 12A, and distal portion or free end 18A extending from the base 20A. In accordance with the invention, the free end 18A has a relatively abrasive surface.

With reference to FIG. 2, it can be seen that the free end 18A tapers inwardly (e.g., narrows) in a direction away from the base 20A moving distally along a central axis 22A extending through the geometric center of the tip portion 14A. The free end 18A of the elastomeric element 16A has a frustoconical configuration while the base 20A of the elastomeric element 16A has a cylindrical configuration. The cylindrical base 20A is configured without the abrasive surface provided on or in the free end 18A.

In one preferred form of the first embodiment of the instrument 10A, the elastomeric element 16A has a total length extending from the handle 12A in the direction along the central axis 22A of about 1.7 mm, with the base 20A having a length of about 0.7 mm and the free end 18A having a length of about 1.0 mm.

In another presently preferred form of the first embodiment of the instrument 10A, the elastomeric element 16A has a total length extending from the handle 12A in the direction along the central axis 22A of about 1.2 mm, with the base 20A having a length of about 0.5 mm and the free end 18A having a length of about 0.7 mm.

In order to effect the desired scraping/abrading action of the instrument 10A, the relatively abrasive surface of the free end 18A comprises an impregnated abrasive composition. The impregnated abrasive composition may comprise diamond particles or abrasive granular or dust particles. Alternatively, the abrasive surface may be provided through subjecting the elastomeric element 16A to a secondary coating process. In yet another alternative, the relatively abrasive surface of the free end 18A is formed from a surface-roughening or texturing of the elastomeric material of the element 16A.

In one presently preferred form of the invention, the free end 18A of the instrument has a surface roughness of between about N8-N12 according to the ISO 1302 Roughness Grade Numbers. In the preferred form, the free end 18A of the tip portion 14A is provided with a fructo-conical configuration when the elastomeric element 16A is formed. Preferably, the elastomeric element 16A is formed from a medical grade silicone material with a durometer of between about 60 and about 90 on the Shore 00 scale, while the hand grip portion 12A of the instrument is formed from a metal or sufficiently stiff plastic or composite material.

The handle portion 12A of the instrument 10A is preferably made of material like malleable nitinol or other malleable alloys or metals and is provided with a tip portion 14A in the form of an elastomeric element 16A having a base 20A, secured to the distal end of the hand grip portion 12A, and a free end 18A extending from the base 20A. Notably, the free end 20A is provided with a relatively abrasive surface, compared to the material of the elastomeric element 16A. The elastomeric element 16A may be secured to the handle portion 12A of the instrument 10A by mechanical fit, overmolding or bi-injection molding, adhesive, welding, or any other suitable means. The elastomeric element 16A may further be removable from the handle portion 12A for replacement.

The instrument 10A is further provided with a movable knife or piercing element 30A. In its retracted position (FIG. 2), the knife element 30A does extend past or through the distalmost point of the free end 18A of the elastomeric element 16A. If the abrasion of the eye is insufficient during operation of the instrument 10A, on its own, to restore sufficient drainage through the eye, then the user of the surgical instrument 10A may extend the knife element 30A (which may be a flat-edged knife, rounded knife, oval knife, spatulated knife, point, etc.) into a moved or extended, operative position (FIG. 3) such that its piercing end 34A extends through and past the free end 18A of the elastomeric element 16A. The user may then pierce the tissues of the eye with the end 34A of the knife element 30A to enhance the drainage therethrough.

The instrument 10A may be a single use instrument that is intended to be discarded after it is used in a surgical procedure. The knife element 30A may therefore be extendable from its retracted position into its moved or operative position and need not be configured to return to its retracted position. The movement mechanism may be any known mechanism, such as a spring-loaded, push-button type mechanism, finger-grip-activated type or any mechanical equivalent thereto. Furthermore, the instrument 10A may employ one or more safety blocking elements or locks to prevent inadvertent movement of the knife element 30A away from the retracted position until the user intends for such movement to occur.

If the instrument 10A is to be a multi-use instrument, which would be sterilized between uses, then the knife element 30A may returnable form its operative position back into its retracted position after use. A catch element, as is known in the art, may be employed to retain the knife element 30A in its retracted position. The instrument 10A may also be made for single-use, disposable type, and/or may be formed from appropriate materials that can be sterilized and subject to Ethylene oxide or Gamma radiation or other sterilizations and that degrades when subjected to steam sterilization.

Preferably, the extension of the knife element 30A from the retracted position toward the operative position is accompanied by some tactile and/or audible feedback (such as a click) to indicate the emergence of some portion of the knife element 30A through the elastomeric element 16A.

The knife element 30A may be formed from a malleable material to enable access to the entirety of the eye.

The inventors of the present invention have found that using an instrument as described herein having a relatively abrasive surface and movable knife element may be advantageous in the restoration of normal or sufficient drainage through the eye by the abrasion of the clogged or blocked areas of the eye.

In one method of operation of the instrument 10A, the user would create two incisions or ports within the eye. The ports are used to accommodate the insertion of the instrument 10A, and the implantation and removal of viscoelastic substances (OVD) from the eye, such as with an irrigation/aspiration instrument or instruments. The ports would be used to fill the anterior chamber of the eye with viscoelastic material to the appropriate viscosity. The instrument 10A into the first port to gently rub the area of the trabecular meshwork, about 120 degrees, with the free end 18A of the tip 14A about three to five times to free or dislodge deposits from the trabecular meshwork. A MORI Goniotomy lens may be used to observe the area being rubbed. The ports would be used to remove the viscoelastic material from the anterior chamber of the eye. The anterior chamber may be filled with balanced salt solution (BSS) to reach the desired intraocular pressure. In one preferred form of the method, the side ports in the eye are formed at the 12 o'clock and 3 o'clock positions. In another preferred form of the method of use of the instrument 10A, the side ports in the eye are formed at the 10 o'clock and 3 o'clock positions, and a third port is formed at the 12 o'clock position to accommodate insertion of an intraocular lens (IOL).

The knife element 30A may be optionally deployed from its retracted position to further dislodge deposits during the above-discussed methods.

Figure 4:
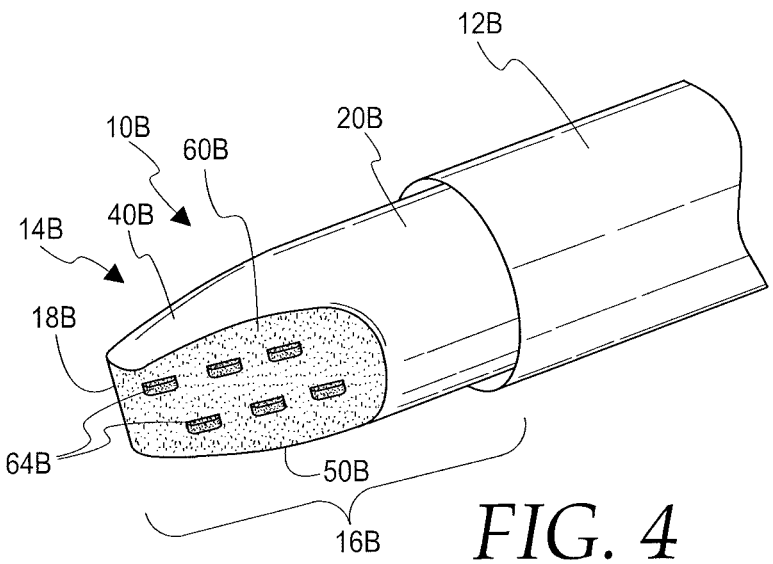
FIG. 4 is an enlarged, fragmentary, perspective view taken from above of a second embodiment of a surgical instrument according to the present invention.

A second embodiment of a goniotomy surgical instrument of the present invention is illustrated in FIG. 4, wherein the instrument is designated generally by the reference number 10B. The numbered features of the second embodiment of the instrument 10B illustrated in FIG. 4 are designated generally with the suffix letter "B" and are analogous to features of the first embodiment of the instrument 10A that share the same number (without the suffix letter "A").

The second illustrated embodiment of the instrument 10B is similar in nature to the first illustrated embodiment of the instrument 10A and includes a hand grip portion 12B having a proximal and distal end with a tip portion 14B extending from the distal end of the hand grip portion 12B. The tip portion 14B comprises an elastomeric element 16B having a base 20B secured to the distal end of the hand grip portion 12B, and a free end 18B extending from the base 20B.

With reference to FIG. 4, the instrument 10B differs from the previously-discussed embodiment of the instrument 10A, in that the instrument 10B has an elastomeric element 16B with a different tapering configuration and has a plurality of abrading features that are thought to more effectively free or dislodge deposits from the tissues around the Schlemm's canal. Specifically, the elastomeric element 16B includes an upper sloping portion 40B and lower sloping portion 50B that are substantially free of any abrasive or roughened surface. The elastomeric element 16B further includes an abrasive band or region 60B on its lateral sides. The abrasive band 60B includes a plurality of protrusions 64B extending outwardly therefrom.

The inventors have found that the instrument 10B having a series of protrusions 64B formed on at least the lateral surfaces of the elastomeric element 16B, may be more effective in restoring the normal drainage, or at least sufficient drainage, through the trabecular meshwork with the abrasion of the clogged or blocked areas of the eye, while presenting only the non-abrasive surfaces against the endothelium. The protrusions 64B are believed to produce a vibrational element or wave-like pattern of indentation of the eye tissues during operation. The instrument 10B may be operated by hand or may be part of a larger device, such as a vibratory, piezoelectric handpiece or other movable handpiece.

In one preferred form of the second illustrated embodiment of the instrument 10B, the protrusions 64B are linear segments that extend in a generally horizontal pattern on the lateral sides of the abrasive band 60B along the central axis of the tip portion 14B. The protrusions 64B may be abrasive or non-abrasive. The protrusions 64B may be integrally formed form an elastomer together with the elastomeric element 16B, or they may be formed from a different, harder material joined or molded with the elastomeric element 16B.

Figure 5:
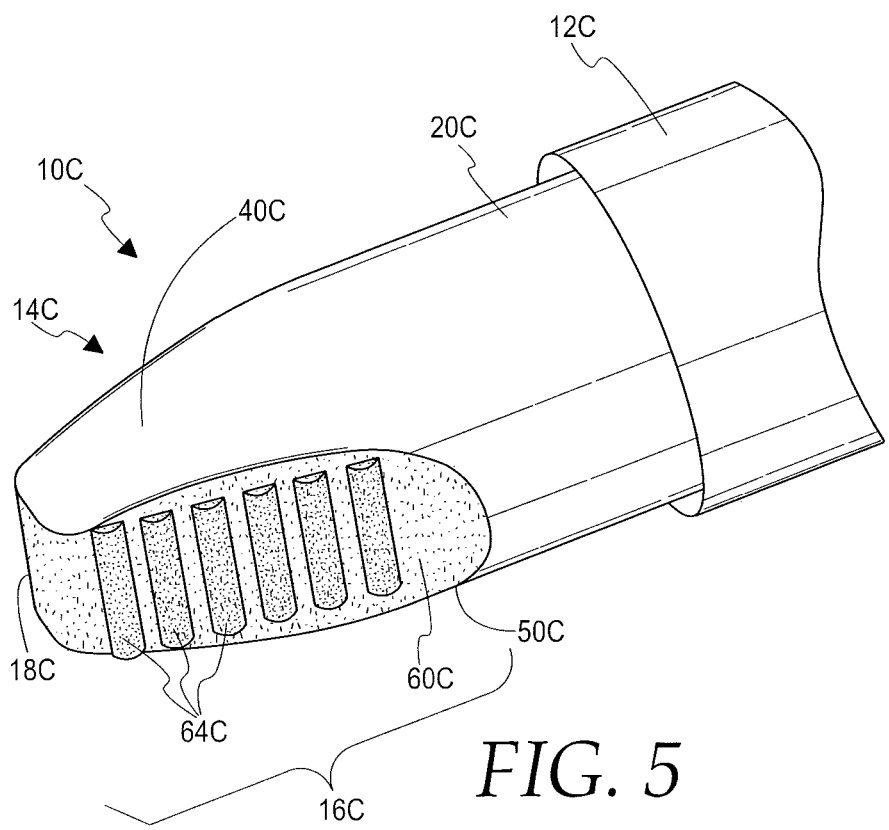
FIG. 5 is a greatly enlarged, fragmentary, perspective view taken from above of a third embodiment of a surgical instrument according to the present invention.

A third embodiment of a goniotomy surgical instrument of the present invention is illustrated in FIG. 5, wherein the instrument is designated generally by the reference number 10C. The numbered features of the third embodiment of the instrument 100 illustrated in FIG. 5 are designated generally with the suffix letter "C" and are analogous to features of the second embodiment of the instrument 10B that share the same number (without the suffix letter "B").

The third illustrated embodiment of the instrument 10C differs from the prior embodiment in that it includes protrusions 64C that are linear segments that extend in a generally vertical pattern on the lateral sides of the abrasive band 60C (i.e., extending between the smooth upper surface 40C and the smooth lower surface 50C of the instrument 10C). The protrusions 64C may be abrasive or non-abrasive. The protrusions 64C may be integrally formed form an elastomer together with the elastomeric element 16C, or they may be formed from a different, harder material that is molded or joined with the elastomeric element 16C.

The arrangement of the protrusions 64C is believed to produce an advantageous vibrational element or wave-like pattern of indentation and release of the eye tissues during operation. The instrument 10C may be operated by hand or may be part of a larger device, such as a vibratory, piezoelectric handpiece or other vibratory handpiece.

Figure 6:
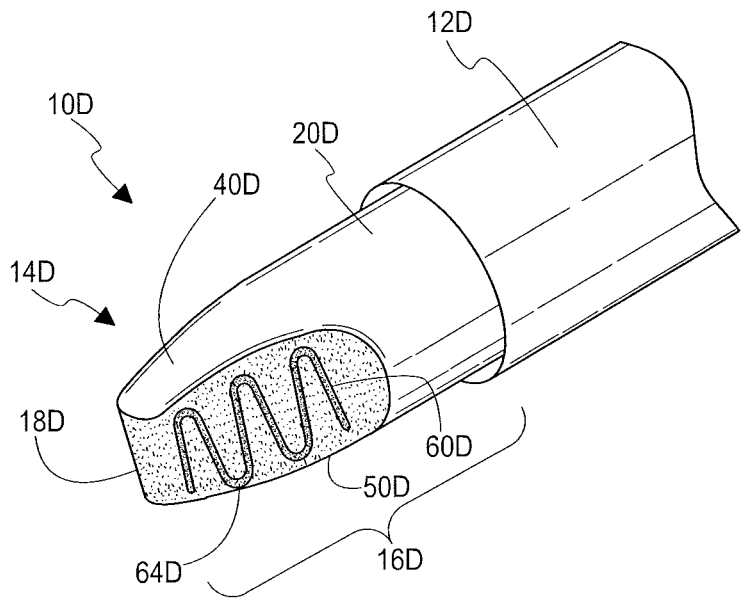
FIG. 6 is an enlarged, fragmentary, perspective view taken from above of a fourth embodiment of a surgical instrument according to the present invention.

A fourth embodiment of a goniotomy surgical instrument of the present invention is illustrated in FIG. 6, wherein the instrument is designated generally by the reference number 10D. The numbered features of the fourth embodiment of the instrument 10D illustrated in FIG. 6 are designated generally with the suffix letter "D" and are analogous to features of the second embodiment of the instrument 10B that share the same number (without the suffix letter "B").

The fourth illustrated embodiment of the instrument 10D differs from the prior embodiment in that it includes protrusions 64D on each of the lateral sides of the abrasive band 60D which extend in a wave-like pattern. The protrusions 64D may be abrasive or non-abrasive. The protrusions 64D may be integrally formed form an elastomer together with the elastomeric element 16D, or they may be formed from a different, harder material joined with the elastomeric element 16D.

The particular arrangement of the protrusions 64D is believed to produce an advantageous vibrational element or wave- like pattern of indentation and release of the eye tissues during operation. The instrument 10D may be operated by hand or may be part of a larger device, such as a vibratory, handpiece.

Figure 7:
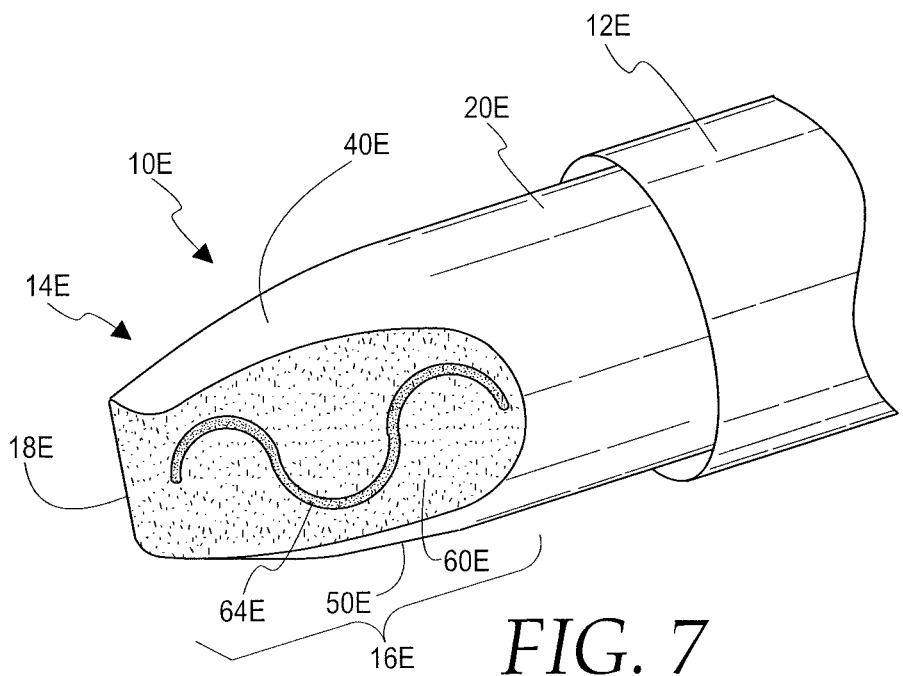
FIG. 7 is a greatly enlarged, fragmentary, perspective view taken from above of a fifth embodiment of a surgical instrument according to the present invention.

A fifth embodiment of a goniotomy surgical instrument of the present invention is illustrated in FIG. 7, wherein the instrument is designated generally by the reference number 10E. The numbered features of the fifth embodiment of the instrument 10E illustrated in FIG. 7 are designated generally with the suffix letter "E" and are analogous to features of the fourth embodiment of the instrument 10D that share the same number (without the suffix letter "D").

The fifth illustrated embodiment of the instrument 10E differs from the prior embodiment in that it includes protrusions 64E on each of the lateral sides of the abrasive band 60E which extend in a gentler, more spaced apart wave-like pattern. The protrusions 64E may be abrasive or non-abrasive. The protrusions 64E may be integrally formed form an elastomer together with the elastomeric element 16E, or they may be formed from a different, harder material joined with the elastomeric element 16E.

The particular arrangement of the protrusions 64E is believed to produce an advantageous vibrational element or wave-like pattern of indentation and release of the eye tissues during operation. The instrument 10E may be operated by hand or may be part of a larger device, such as a vibratory, piezoelectric handpiece.

The inventors have further determined that it may further be advantageous to combine any one of the instruments disclosed herein with an irrigation system and an aspiration system. For example, the instruments may be incorporated into an aspiration/irrigation handpiece to supply irrigating liquids to the eye in order to aid in flushing and aspirating dislodged particles in the eye during the use of the instruments.

It will further be understood that the instruments disclosed herein may be incorporated into a larger machine or device, whereby the hand grip portion is connected to such a machine or device, and may be controlled, operated, or manipulated by such a machine or device and not necessarily by hand.

In some applications, the above-discussed protrusions may have a different form, such as discrete rounded features projecting from the free end of the elastomeric element. Other shapes, polygonal, or irregular, may be suitable. It will be understood that the protrusions need not be symmetric on the elastomeric element. For example, one lateral side may have a different arrangement of protrusions than the other, opposite lateral side. Further, one lateral side may have no protrusions, while the opposite lateral side has at least one protrusion thereon.

In still other applications, the instruments disclosed herein (or at least a portion thereof) may be formed from a material that is malleable, such as a metal, wire, or polymer, which may be bent by a user to hold its position for better manipulation of the instrument by the user. For example, the hand grip portion may be formed from a malleable metal that may be selectively bent by a user during different uses of the instrument to reach different locations of the target areas of the eye.

Figure 8:
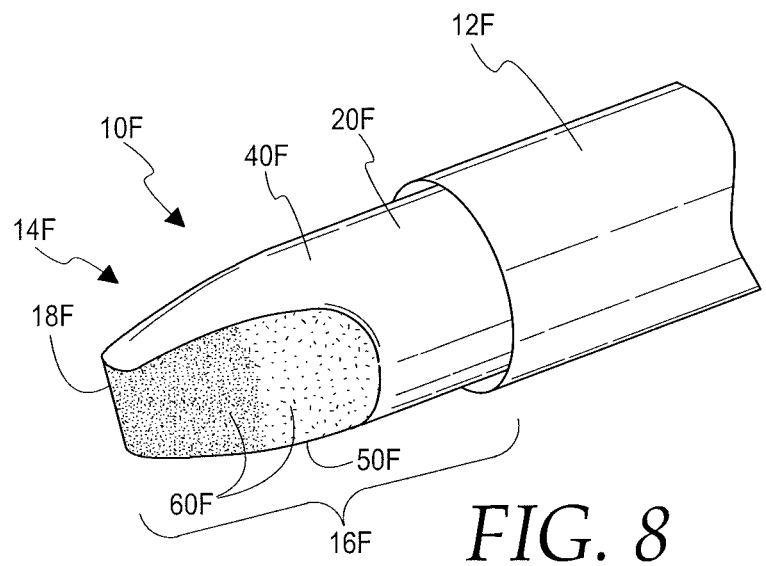
FIG. 8 is an enlarged, fragmentary, perspective view taken from above of a sixth embodiment of a surgical instrument according to the present invention.

A sixth embodiment of a goniotomy surgical instrument of the present invention is illustrated in FIG. 8, wherein the instrument is designated generally by the reference number 10F. The numbered features of the sixth embodiment of the instrument 10F illustrated in FIG. 8 are designated generally with the suffix letter "F" and are analogous to features of the fifth embodiment of the instrument 10E that share the same number (without the suffix letter "E").

The sixth illustrated embodiment of the instrument 10F differs from the prior embodiment in that it includes a first and second, opposite abrasive bands or surfaces 50F and 60F on each of the lateral sides of the tip portion 14F of the instrument 10F, and the surfaces 50F and 60F are devoid of any protrusions. Furthermore, the roughened surfaces 60F and 50F have discrete sections or zones (visible in FIG. 8) with different grades of surface roughnesses which may be selectively utilized by the user during use of the instrument 10F. Only the demarcation between zones of the roughened surface 60F is visible in FIG. 8, and it will be understood that the opposite side (surface 50F) would include an identical demarcation. It will be further understood that the instrument 10F may include a tip portion 14F with more than two sections of varying roughnesses on the surfaces 50F and/or 60F. The roughness of the surfaces 50F and 60F may be formed by sandblasting, glass-bead blasting, or other blasting of the elastomeric element 16F or formed by impregnation of a grit-like substance (diamond dust, particulates within the elastomeric element 16F etc.).

While the zones of differing roughnesses of the surface 60F are shown as divided by a discrete line or demarcation, it will be understood that the transition in roughness between the two sections may instead be a gradient. The different sections may be color coded in different colors or obvious textures to assist the user in selecting the appropriate surface for use against the eye for the preferred massaging effect.

Figure 9:
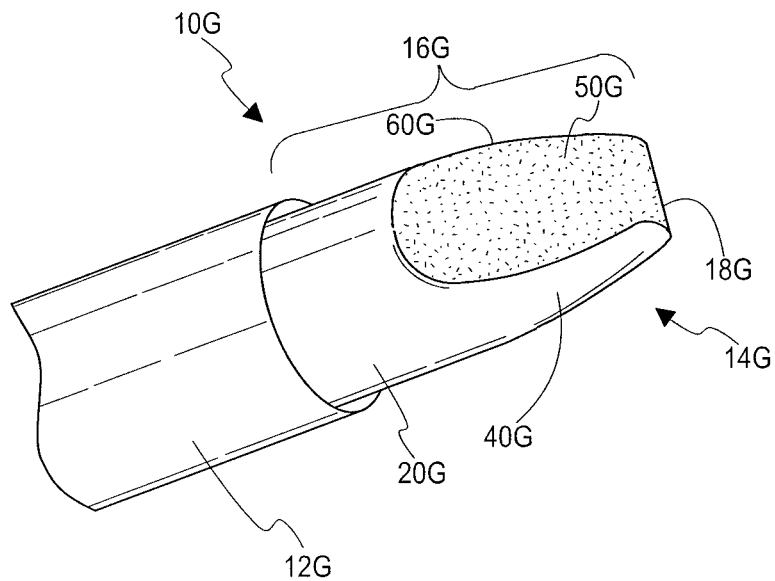
FIG. 9 is an enlarged, fragmentary, perspective view taken from above of a seventh embodiment of a surgical instrument according to the present invention.

A seventh embodiment of a goniotomy surgical instrument of the present invention is illustrated in FIG. 9, wherein the instrument is designated generally by the reference number 10G. The numbered features of the seventh embodiment of the instrument 10G illustrated in FIG. 8 are designated generally with the suffix letter "G" and are analogous to features of the sixth embodiment of the instrument 10F that share the same number (without the suffix letter "F").

The seventh illustrated embodiment of the instrument 10G differs from the prior embodiment in that it includes a first and second, opposite abrasive bands or surfaces 50G and 60G on each of the lateral sides of the tip portion 14G of the instrument 10F, and the surfaces 50G and 60G are roughened to varying degrees of surface roughness. For example, a left side of the instrument containing roughened surface 50G may be significantly rougher than a right side of the instrument containing the roughened surface 60G when the instrument 10G is held by the user. It will be further understood that the instrument 10G may include a tip portion 14G rotated such that the top side of the instrument contains the roughened surface 50G while the bottom side of the instrument contains the roughened surface 60G, or vice versa, when the instrument 10G is held by the user. The roughness of the surfaces 50G and 60G may be formed by sandblasting, glass-bead blasting, or other blasting of the elastomeric element 16G or formed by impregnation of a grit-like substance (diamond dust, particulates within the elastomeric element 16G etc.).

While the roughnesses of the surface 50G and 60G are shown as a consistent roughness in FIG. 9, it will be understood that the roughnesses of these surfaces 50G and 60G may vary (e.g., two or more sections or gradients, as discussed above). The different surfaces 50G and 60G may be color coded in different colors or obvious textures to assist the user in selecting the appropriate surface for use against the eye for the preferred massaging effect.

The instrument 10G may be operated by hand or may be part of a larger device, such as a vibratory, piezoelectric handpiece, as will be discussed in greater detail hereinafter.

Figure 10:
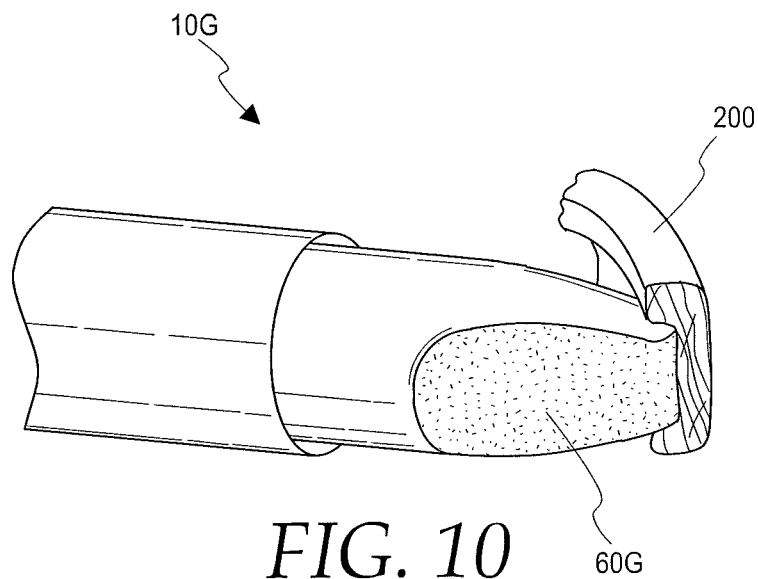
FIG. 10 is an enlarged, fragmentary, diagrammatic view of the instrument of FIG. 9 shown in contact with the tissues of the eye proximate.

With reference now FIG. 10, the operative, distal end of the instrument 10G is shown diagrammatically in engagement with the tissues of the eye proximal to the trabecular meshwork and/or the Canal of Schlemm 200. The rough sandblasting of the surface 60G favors a massaging effect on the tissues to free or dislodge possible 'clogs' or deposits and massage the tissue to facilitate better flow that helps in reducing the intra-ocular pressure (10P). Increased 10P can lead to permanent blindness, caused in cases of patients suffering with glaucoma or other diseases that cause the blockage of the Canal. It will be understood that the other instruments discussed herein would function similarly.

Figure 14:
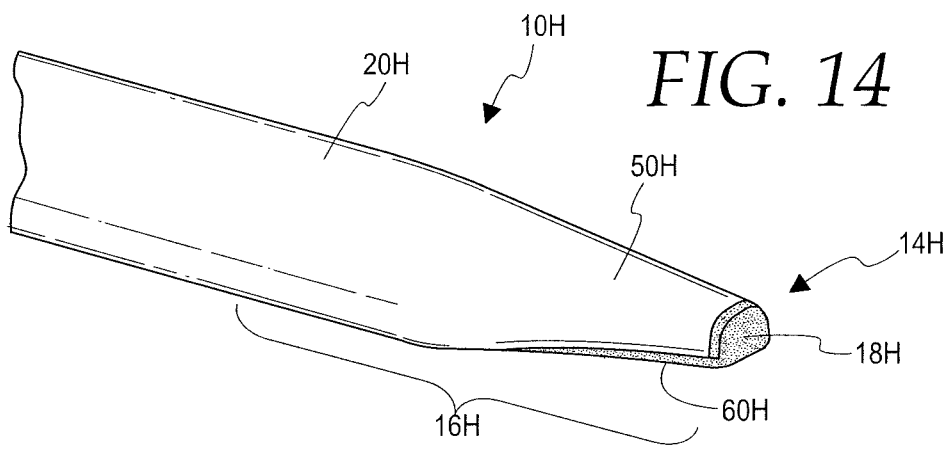
FIG. 14 is an enlarged, fragmentary, perspective view taken from above of an eighth embodiment of a surgical instrument according to the present invention.
Figure 15:
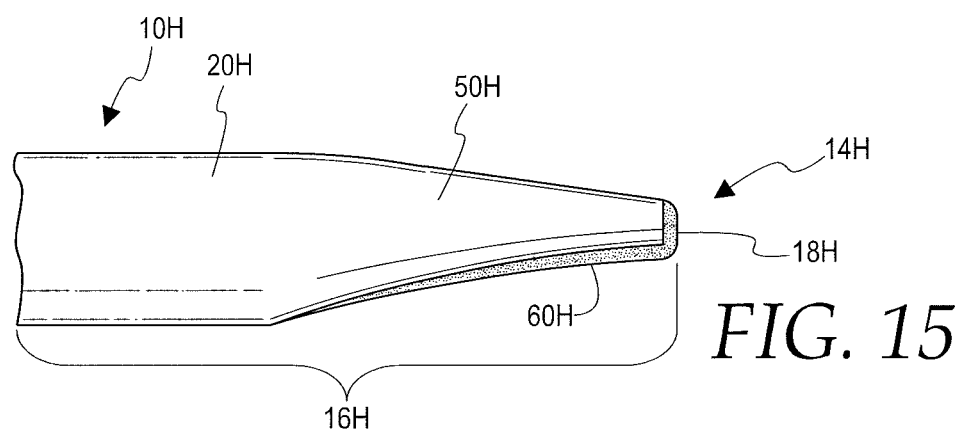
FIG. 15 is an enlarged, fragmentary, perspective view taken from above and on the right side of the instrument shown in FIG. 14.
Figure 16:
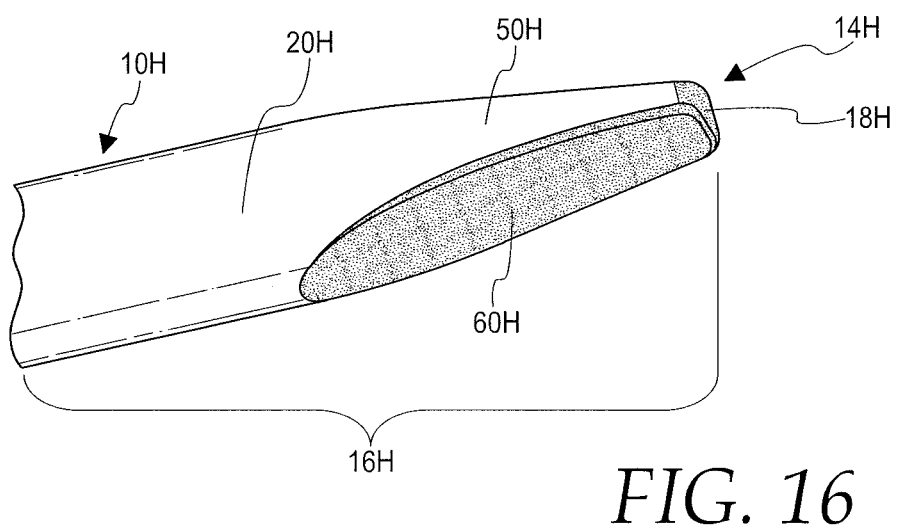
FIG. 16 is an enlarged, fragmentary, perspective view taken from below and on the right side of the instrument shown in FIG. 14.
Figure 17:
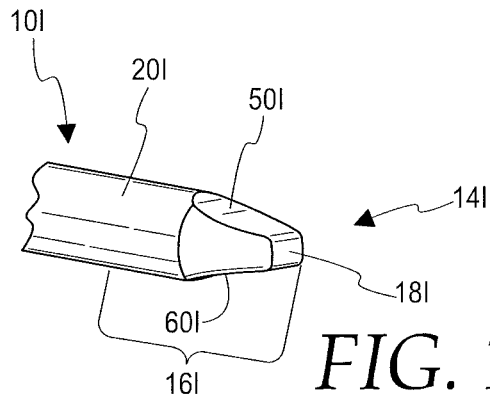
FIG. 17 is an enlarged, fragmentary, perspective view taken from above and on the right side of a ninth embodiment of a surgical instrument according to the present invention.
Figure 18:
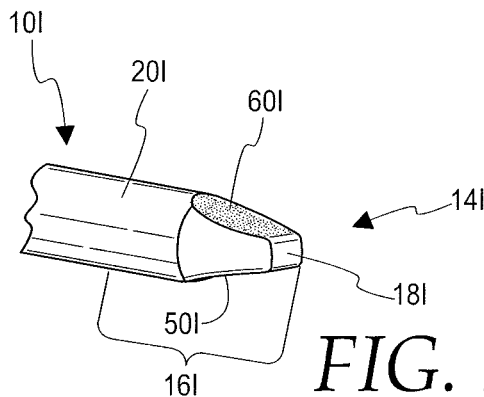
FIG. 18 is an enlarged, fragmentary, perspective view taken from below and on the left side of the instrument shown in FIG. 17.

An eighth embodiment of a goniotomy surgical instrument of the present invention is illustrated in FIGS. 14-16, wherein the instrument is designated generally by the reference number 10H. The numbered features of the eighth embodiment of the instrument 10H illustrated in FIGS. 14-16 are designated generally with the suffix letter "H" and are analogous to features of the seventh embodiment of the instrument 10G that share the same number (without the suffix letter "G").

The eighth illustrated embodiment of the instrument 10H differs from the prior embodiment in that it includes a relatively smooth, non-abrasive surface 50H on the distal or free end 18H of the tip portion 14H of the elastomeric element 16H and an opposite, first abrasive surface 60H. The first abrasive surface 60H is concave and faces downward or on the bottom of the tip portion 14H (with the instrument 10H held in the hand of the user). The smooth surface 50H connects to the proximal portion 20H of the elastomeric element 16H, and it is convex and faces upward or on top of the tip portion 14H. The distalmost or terminal portion of the free end 18H has a blunted, semicircular shape and is preferably roughened to the same extent as the surface 60H. The roughness of the surface 60H may be formed by sandblasting, glass-bead blasting, or other blasting of the elastomeric element 16H or formed by impregnation of a grit-like substance (diamond dust, particulates within the elastomeric element 16H etc.).

The inventors have found that the instrument 10H having a downwardly-facing concave roughened surface 60H and an upwardly-facing smooth surface 50H may be more effective in restoring the normal drainage, or at least sufficient drainage, through the trabecular meshwork with the abrasion of the clogged or blocked areas of the eye, while presenting only a non-abrasive surface against the endothelium and other delicate structures of the eye.

A ninth embodiment of a goniotomy surgical instrument of the present invention is illustrated in FIGS. 17-20, wherein the instrument is designated generally by the reference number 10I. The numbered features of the ninth embodiment of the instrument 10I illustrated in FIGS. 17-20 are designated generally with the suffix letter "I" and are analogous to features of the seventh embodiment of the instrument 10G that share the same number (without the suffix letter "G").

The ninth illustrated embodiment of the instrument 10I differs from the prior discussed seventh embodiment of the invention in that the instrument 10I includes a relatively smooth, non-abrasive surface 50I on the distal or free end 18I of the tip portion 14I and an opposite, first abrasive surface 60I. The first abrasive surface 60I is concave and faces downward or on the bottom of the tip portion 14I. The smooth surface 60I connects to the proximal portion 20I of the elastomeric element 16I, and it is also concave and faces upward or on top of the tip portion 14I. The distalmost portion of the free end 18I has a rounded, blunted symmetrical shape and is preferably smoothed to the same extent as the surface 60I. The roughness of the surface 60I may be formed by sandblasting, glass-bead blasting, or other blasting of the elastomeric element 16I or formed by impregnation of a grit-like substance (diamond dust, particulates within the elastomeric element 16I etc.).

Figure 19:
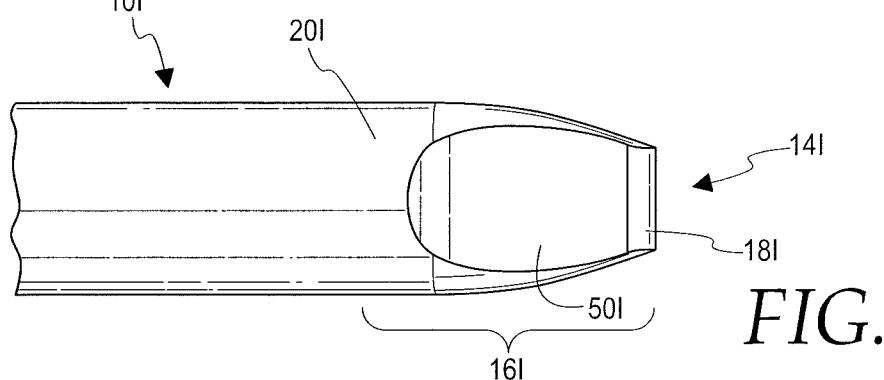
FIG. 19 is a greatly enlarged, fragmentary, top plan view of the instrument shown in FIG. 17 showing the smooth top surface of the free end of the instrument.
Figure 20:
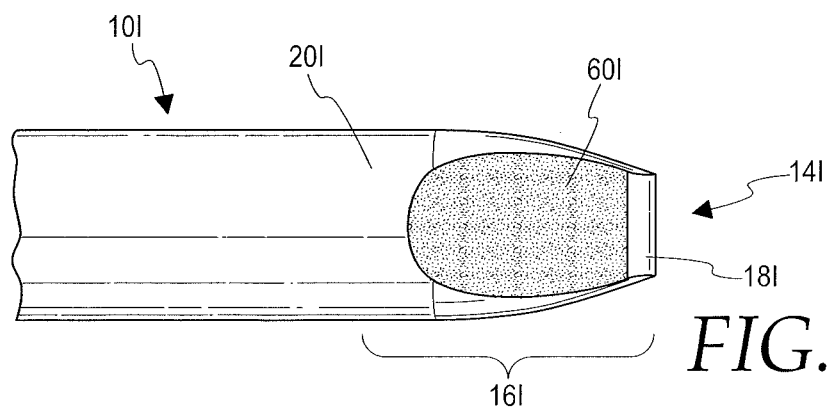
FIG. 20 is a greatly enlarged, fragmentary, bottom plan view of the instrument shown in FIG. 17 showing the roughened surface of the free end of the instrument.

As can be seen in each of FIGS. 19 and 20 each of the first relatively abrasive surface 60I and the smooth surface 50I has a generally horseshoe shape with a closed, arcuate proximal portion and an open distal portion (in the direction from the hand grip of the instrument toward the cantilevered, tip portion 14I).

Figure 21:
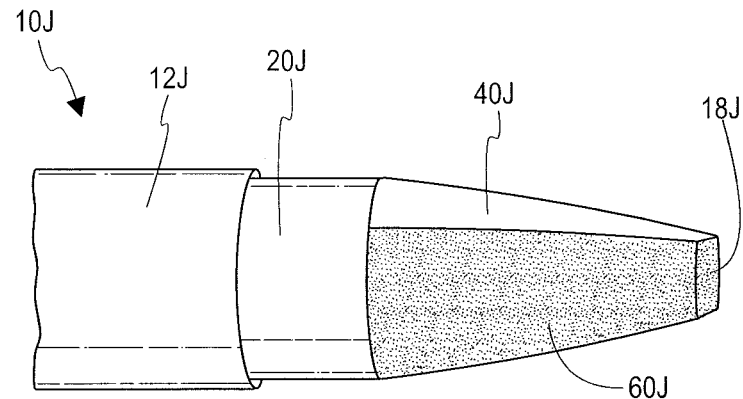
FIG. 21 is a greatly enlarged, fragmentary, perspective view taken from above and on the right side of a tenth embodiment of a surgical instrument according to the present invention.
Figure 22:
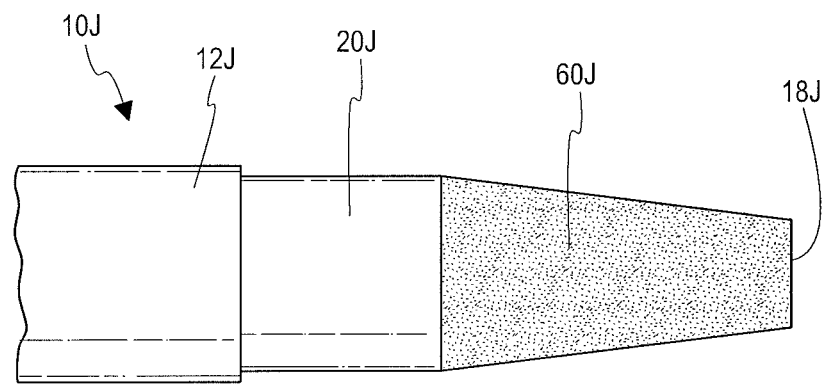
FIG. 22 is a greatly enlarged, fragmentary, right side elevation view of the instrument shown in FIG. 21.
Figure 23:
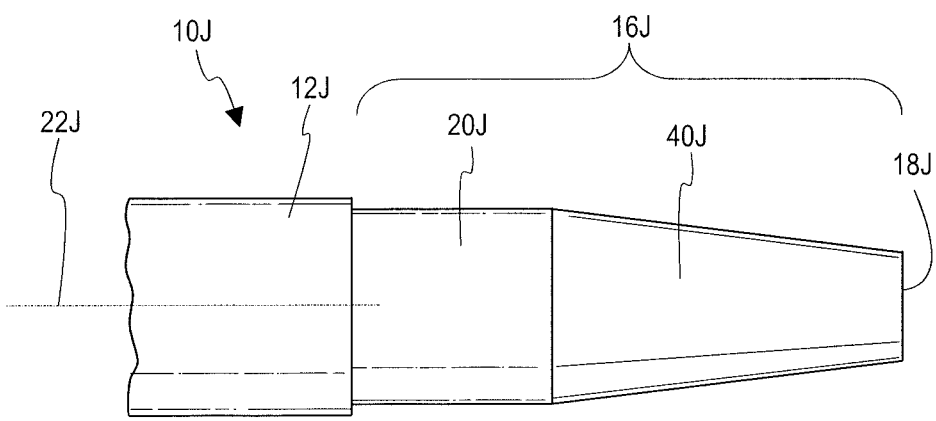
FIG. 23 is a greatly enlarged, fragmentary, top plan view of the instrument shown in FIG. 21.

A tenth embodiment of a goniotomy surgical instrument of the present invention is illustrated in FIGS. 21-23, wherein the instrument is designated generally by the reference number 10J. The numbered features of the tenth embodiment of the instrument 10J illustrated in FIGS. 21-23 are designated generally with the suffix letter "J" and are analogous to features of the second embodiment of the instrument 10B that share the same number (without the suffix letter "B").

The tenth illustrated embodiment of the instrument 10J differs from the prior discussed second embodiment of the invention in that the instrument 10J includes an elastomeric element 16J and tip portion 14J having the form of a pyramidal frustum that tapers along the central geometric axis 22J (FIG. 23 only). The elastomeric element 16J is affixed to the instrument handle portion 12J by a generally uniform cross-sectional shape base portion 20J and terminates in a rectangular or square blunted, free end 18J. The pyramidal frustum includes relatively smooth, non-abrasive top and opposite, bottom sides or surfaces 40J (top surface being visible in FIGS. 21 and 23) and a relatively abrasive, opposite lateral surfaces 60J (right side surface visible in FIGS. 21 and 22). The distalmost portion of the free end 18J is preferable roughened to the same extent as the surface 60J. The roughness of the surfaces 60J and 18J may be formed by sandblasting, glass-bead blasting, or other blasting of the elastomeric element 16J or formed by impregnation of a grit-like substance (diamond dust, particulates within the elastomeric element 16J etc.). In one presently preferred form of the invention, the total length of the elastomeric element 16J that extends axially beyond the handle portion 12J is between about 1.0 and 3.0 mm, and more preferably is about 1.4 mm. In the preferred form, the base portion 20J is about 0.52 mm for being affixed to a 23G handle portion 12J, with the free end 18J terminating in the form of a 0.2×0.2 mm square.

The inventors have found that the total length of the elastomeric element that extends axially beyond the handle portion of the preceding embodiments of the instrument should be greater than 1.0, and is preferably at least 1.4 mm. The inventors have further found that the elastomeric element should be formed from a medical grade silicone, TPE, TPE, or like material with a durometer of between about 30 and about 75 on the Shore 00 scale while the hand grip portion of the instrument is formed from a metal or sufficiently stiff plastic or composite material. The free end of the instruments should have a surface roughness of between about N8-N 12 according to the ISO 1302 Roughness Grade Numbers.

In other forms of the invention, at least the tip portion 14A, 14B, 14C, 14D, 14E, 14F, 10G, 10H, 10I, 10J of the instrument may be removable from the remaining portion of the instrument for disposal, replacement, cleaning, and/or other modification. (retractable for improved entry into the incision, safety). In still other forms of the present invention, the tip portion 14, 14A, 14B, 14C, 14D, 14E, 14F, 14G, 14H, 14I, 14J may be wholly retractable within the handle portion or hand grip portion of the instrument, and may be extended beyond the handle portion by the user after the instrument has been inserted to the target area in the eye to offer improved safety.

Figure 11:
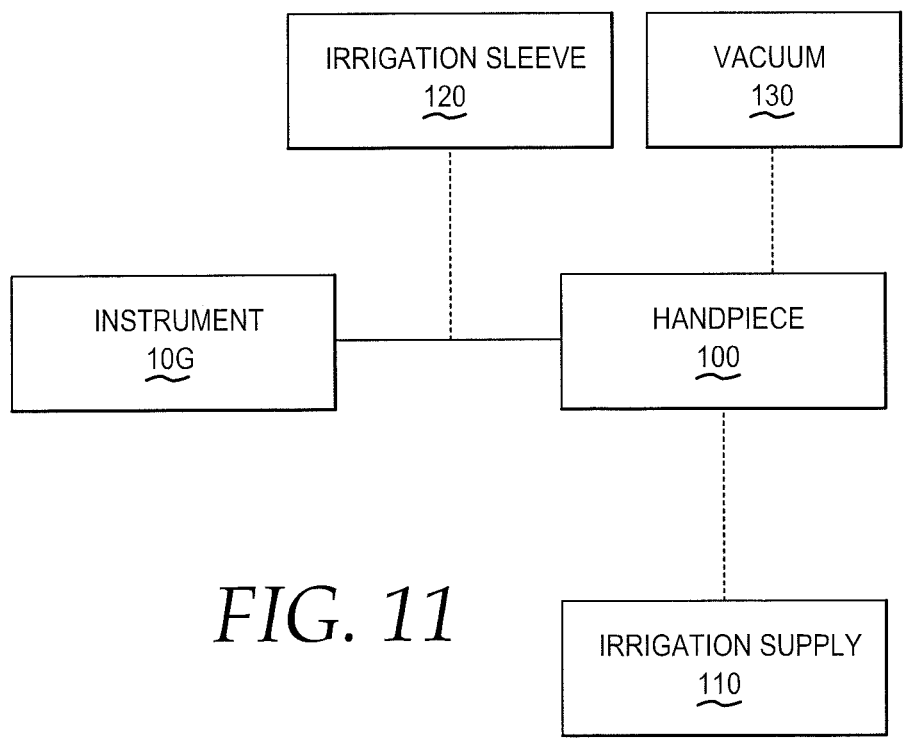
FIG. 11 is a diagrammatic view of the instruments of the present invention in combination with a handpiece, and optionally in combination with an irrigation fluid supply, and further optionally in combination with an irrigation sleeve and a vacuum source.

With reference to FIG. 11, in another broad form of the invention, each of the instruments 10, 10A, 10B, 10C, 10D, 10E, 10F, 10G, 10H, 10I, 10J disclosed herein is capable of being attached or otherwise coupled with a movable or vibratory handpiece 100 to assist in performing the goniotomy procedure. The handpiece 100 may be, for example, a longitudinally-vibrating phacoemulsification handpiece, a torsionally-vibrating phacoemulsification handpiece, an elliptically-vibrating phacoemulsification handpiece, a phacoemulsification handpiece configured for vibratory movement in three dimensions, a vitrectomy handpiece, a piezo electric handpiece, an ultrasound handpiece, a solenoid valve handpiece, pneumatic, or a battery powered handpiece. Other vibratory handpieces may be used with the instruments disclosed herein.

The handpiece 100 may be developed for the treatment of Open Angle Glaucoma, specifically at the Juxtacanalicular Space (JCS), but not limited to, or based on, combination treatments including vibrating, pulsating, oscillating, Guillotine, Piezo, Radiofrequency (RF), Neodymium-doped yttrium aluminum garnet (Nd:YAG) Laser platforms with specially designed tips and/or Laser probes.

The proximal end or portion of the instrument would not function as a hand grip, per se, when incorporated into a handpiece 100 that is gripped by a user, and the proximal portion of the instrument may be removably or non-removably coupled with the handpiece 100, such as by mating threads, luer lock, force fit, snap-fit, etc.

Figure 12:
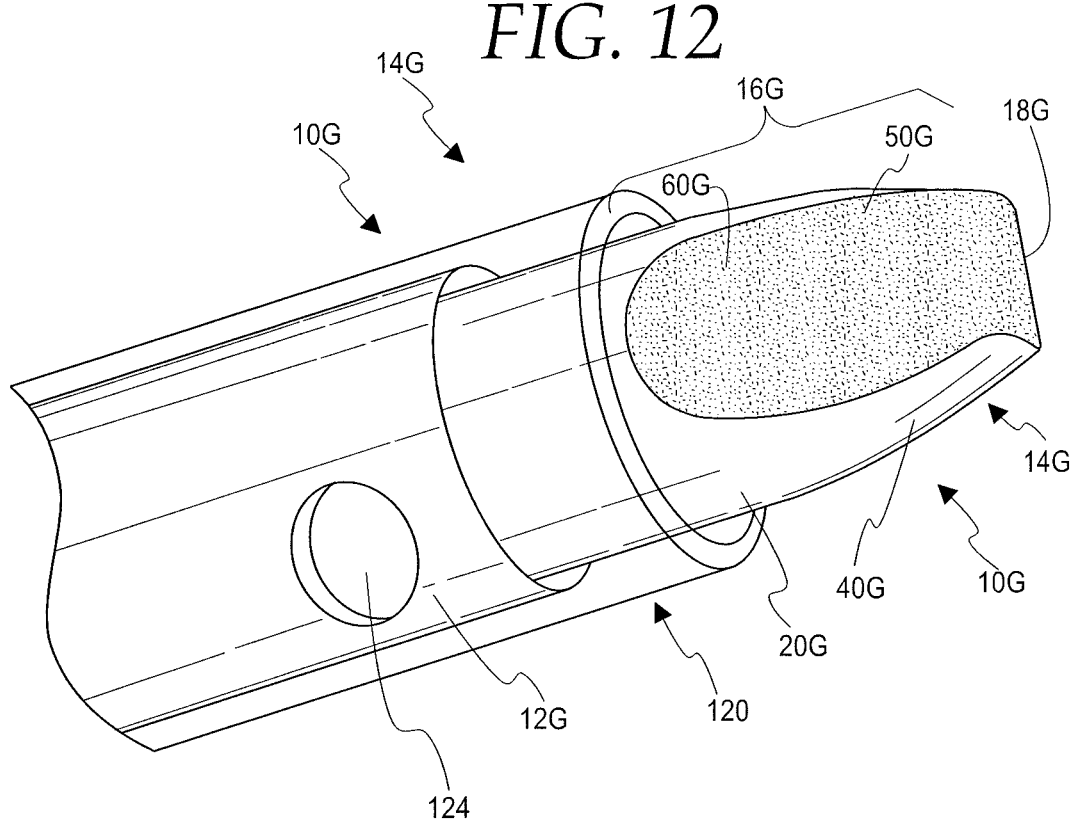
FIG. 12 is an enlarged, fragmentary, perspective view of the instrument of FIG. 9 shown in combination with a fragmentary portion of an irrigation fluid infusion sleeve.
Figure 13:
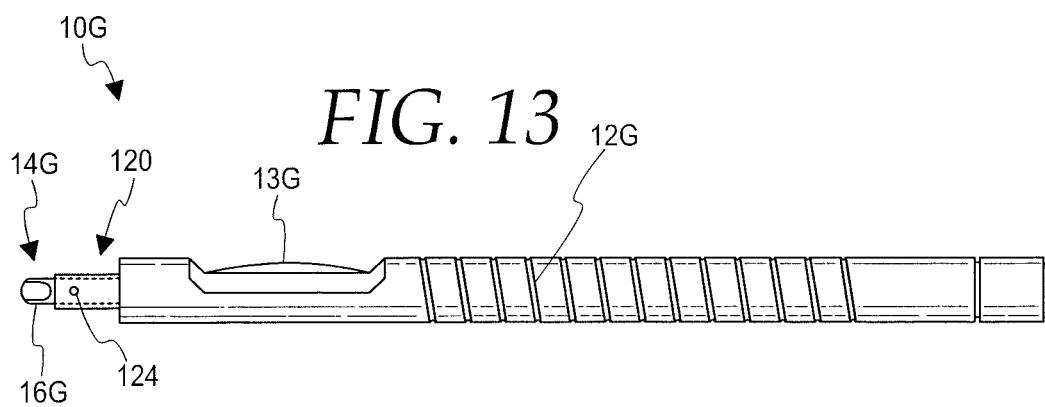
FIG. 13 is a side elevation view of the entire surgical instrument of FIG. 9.

In some applications, the goniotomy surgical instruments 10, 10A, 10B, 10C, 10D, 10E, 10F, 10G, 10H, 10I, 10J disclosed herein may be coupled with an irrigation fluid supply source 110 to provide an irrigation fluid either (i) through one or more cannulas in the instruments, or (ii) around the exterior surface of the tip portion of the instruments when coupled with an irrigation sleeve 120 arranged around a portion of the distal end of the instrument. FIGS. 12 and 13 illustrate the instrument 10G or portions thereof assembled with an irrigation sleeve 120 having a pair of opposing ports or apertures 124 (only one being visible in FIGS. 12 and 13). The instrument handle 12G includes a reservoir for storing an irrigation fluid or other fluid which may be selectively released in a pulse or jet through or around the instrument 10G when a flexible switch or button 13G (FIG. 13) is depressed to increase pressure within the reservoir to send a jet or jets of the fluid to massage the Schlemm's canal or trabecular meshwork tissues. The sleeve 120 may have only one aperture or port 124 or may have more than two apertures or ports 124 in some applications to direct the flow of irrigation fluid in different directions. In some applications, the goniotomy surgical instruments 10, 10A, 10B, 100, 10D, 10E, 10F, 10G, 10H, 10I, 10J disclosed herein may be coupled with a vacuum generator (shown diagrammatically as 130 in FIG. 11) to provide aspiration of fluids or tissues either (i) through one or more cannulas in the instruments, or (ii) around the exterior surface of the tip portion of the instruments.

Other features and advantages will be readily apparent from the following the accompanying drawings and the appended claims.

The invention claimed is:

1. A method for improvement of the drainage of fluid of the eye, wherein the method comprises the steps of:
   obtaining a surgical instrument comprising:
   a hand grip portion having an elongated configuration, having proximal and distal ends,
   a tip portion extending from the distal end of said hand grip portion,
   said tip portion comprising an elastomeric element having a base secured to said distal end of said hand grip portion, and a tapered free end extending from said base,
   said free end configured to massage the trabecular meshwork of the eye; and
   contacting the trabecular meshwork of the eye with said tapered free end of said elastomeric element to massage the trabecular meshwork to dislodge deposits within the trabecular meshwork.

* * * * *